US009719859B2

(12) United States Patent
Kusunose et al.

(10) Patent No.: US 9,719,859 B2
(45) Date of Patent: Aug. 1, 2017

(54) INTERFEROMETER AND PHASE SHIFT AMOUNT MEASURING APPARATUS WITH DIFFRACTION GRATINGS TO PRODUCE TWO DIFFRACTION BEAMS

(71) Applicant: Lasertec Corporation, Yokohama, Kanagawa (JP)

(72) Inventors: Haruhiko Kusunose, Kanagawa (JP); Kiwamu Takehisa, Kanagawa (JP)

(73) Assignee: LASERTEC CORPORATION, Yokohama, Kanagawa (JP)

( * ) Notice: Subject to any disclaimer, the term of this patent is extended or adjusted under 35 U.S.C. 154(b) by 218 days.

(21) Appl. No.: 14/565,703

(22) Filed: Dec. 10, 2014

(65) Prior Publication Data

US 2015/0204729 A1 Jul. 23, 2015

(30) Foreign Application Priority Data

Jan. 22, 2014 (JP) ................................ 2014-009565

(51) Int. Cl.
*G01B 9/02* (2006.01)
*G01J 9/02* (2006.01)
(Continued)

(52) U.S. Cl.
CPC ............ *G01J 9/02* (2013.01); *G01B 9/02041* (2013.01); *G01B 9/02049* (2013.01);
(Continued)

(58) Field of Classification Search
CPC G01J 9/02; G01J 2009/0219; G01B 9/02041; G01B 9/02049; G01B 9/02098;
(Continued)

(56) References Cited

U.S. PATENT DOCUMENTS 5,995,224 A * 11/1999 de Groot ................ G01B 11/30 356/511
6,445,182 B1 9/2002 Dean et al.
(Continued)

FOREIGN PATENT DOCUMENTS

JP S63-298107 A 12/1988
JP H04-315009 A 11/1992
(Continued)

OTHER PUBLICATIONS

Japanese Patent Application No. 2014-009565: Office Action mailed on Dec. 18, 2014.

(Continued)

*Primary Examiner* — Hwa Lee
(74) *Attorney, Agent, or Firm* — Procopio, Cory, Hargreaves & Savitch LLP

(57) ABSTRACT

The present invention is directed to the provision of an interferometer and a phase shift amount measuring apparatus that can precisely operate in the EUV region. The interferometer according to the invention comprises an illumination source for generating an illumination beam, an illumination system for projecting the illumination beam emitted from the illumination source onto a sample, and an imaging system for directing the reflected beam by the sample onto a detector. The illumination system includes a first diffraction grating for producing a first and second diffraction beams which respectively illuminate two areas on the sample where are shifted from each other by a given distance, and the imaging system includes a second grating for diffracting the first and second diffraction beams reflected by the sample to produce a third and fourth diffraction beams which are shifted from each other by a given distance.

12 Claims, 12 Drawing Sheets

(51) Int. Cl.

| | |
|---|---|
| ***G01N 21/45*** | (2006.01) |
| ***G03F 1/26*** | (2012.01) |
| ***G03F 1/84*** | (2012.01) |

(52) U.S. Cl.
CPC ......... *G01B 9/02098* (2013.01); *G01N 21/45* (2013.01); *G03F 1/26* (2013.01); *G03F 1/84* (2013.01); *G01B 2290/30* (2013.01); *G01J 2009/0219* (2013.01)

(58) Field of Classification Search
CPC ......... G01B 2290/30; G03F 1/84; G03F 1/26; G01N 21/45
See application file for complete search history.

(56) References Cited

U.S. PATENT DOCUMENTS

| | | | | |
|---|---|---|---|---|
| 2003/0144819 | A1* | 7/2003 | Takeuchi | G03F 7/706 702/189 |
| 2005/0046866 | A1 | 3/2005 | Miura et al. | |
| 2008/0231862 | A1 | 9/2008 | Haidner et al. | |

FOREIGN PATENT DOCUMENTS

| | | | |
|---|---|---|---|
| JP | 2003-222572 | A | 8/2003 |
| JP | 2005-049317 | A | 2/2005 |
| JP | 2005-083974 | A | 3/2005 |
| JP | 2009-506335 | A | 2/2009 |
| WO | WO99/56159 | A | 11/1999 |

OTHER PUBLICATIONS

Japanese Patent Application No. 2014-009565: Office Action mailed on Sep. 24, 2014.

European Patent Application No. 14197869.2: Extended European Search Report mailed on May 29, 2015.

Visser M et al:"A shearing interferometer to characterize EUV optics with a laser plasma source", International Society for Optical Engineering, US, vol. 3997, Jan. 1, 2000, pp. 733-739, XP002253285.

* cited by examiner

Processor
10
11
12
13
14
15
16
16a
16b
16c
17
18
19
20
21
22
23
24 illuminated areas on the sample
−21-th
−20-th
0-th order
+20-th
+21-th
monitor pattern −21-th diffraction image
−20-th diffraction image
0-th order image
+20-th diffraction image
+21-th diffraction image combined image
fiel of view of detector

+

INTERFEROMETER AND PHASE SHIFT AMOUNT MEASURING APPARATUS WITH DIFFRACTION GRATINGS TO PRODUCE TWO DIFFRACTION BEAMS

INCORPORATION BY REFERENCE

This application is based upon and claims the benefit of priority from Japanese patent application No. 2014-009565, filed on Jan. 22, 2014, the disclosure of which is incorporated herein in its entirety by reference.

BACKGROUND OF THE INVENTION

1. Field of the Invention

The present invention relates to an interferometer and a phase shift amount measuring apparatus which are suitable for EUV (Extremely Ultraviolet) lithography.

2. Description of Related Art

In accordance with the refinement of the semiconductor device, the development of the EUV lithography (EUVL) has been strongly demanded. In the EUVL, an EUV radiation source producing an EUV radiation beam whose wavelength is 13.5 nm is used as the exposure source, and a photomask of reflection type (an EUV mask) is used as the mask. The photomask of reflection type comprises a substrate, a reflection film of a multilayer structure consisting of silicon layers and molybdenum layers formed on the substrate, and absorber patterns formed on the reflection film and functioning as a shielding pattern. In the EUVL, since the exposure beam is projected onto the photomask at the incident angle of 6°, the absorber pattern forms a shadow and thus the degradation of resolution has been pointed out. In order to overcome such problem, it is preferable to thin the thickness of the absorber pattern still more. However, if the thickness of the absorber pattern becomes thinner, its reflectance does not become zero, and thus the absorber pattern may become the shielding pattern similar to the half-tone film which has been used in the phase shift mask of half-tone type. By such a reason, it has been focused on a method in which the absorber pattern for introducing a phase difference of λ/2 between the reflected beams by the absorber pattern and by the surrounding reflection film is provided on the reflection film. If the absorber pattern for introducing the phase difference of λ/2 is formed on the reflection film, the reflected radiations by the absorber pattern and by the reflection film are cancelled each other, and thus the EUVL having high resolution can be established. While, on the other hand, the problem arises that the resolution of the EUVL is degraded if the phase difference caused by the absorber pattern shifts from λ/2. Therefore, in the EUVL, there is urgent need to develop a phase shift amount measuring apparatus which can accurately measure the phase shift amount of the absorber pattern.

As the apparatus for measuring the phase shift amount of the photomask, a measuring apparatus using a Mach-Zender interferometer and a wavefront detecting method has been known (for example, see PLT 1). In this known phase shift amount measuring apparatus, the light source for generating a DUV beam is used as the illumination source, and the illumination beam emitted from the light source is projected onto the rear surface of the photomask through a diffraction grating to form laterally shifted beams. The transmitted beam through the photomask is directed onto the Mach-Zender interferometer. The transmitted beam incident on the Mach-Zender interferometer is divided into two beams by a beam splitter of transflective type. The fringe-scan is performed by a double wedge prism arranged on one optical path to introduce the phase modulation of one period. The two beams are combined by a second beam splitter to form an interference beam. The interference beam is received by a two-dimensional imaging device, and then the phase shift amount is calculated on the basis of the phase shift method using the introduced phase modulation amount and the image signal supplied from the imaging device. In the known phase shift amount measuring apparatus, the phase shift amount is obtained based on the wavefront detection method by using the fringe-scan, and therefore high measurement resolution is obtained without complicate calculation process.

An interference measuring apparatus using two diffraction gratings is also known (for example, see PLT 2). In the known measuring apparatus, incoherent light beam is projected toward the diffraction grating (coherent mask 1) which is arranged at the pupil position of the imaging optical component 2. The diffracted beams of 0-th and +1-th emitted from the grating 1 are projected onto the phase shift mask 4 of transmission type to form an interferogram. The formed interferogram is imaged on another diffraction grating 3 and further is imaged on the detector through the second imaging optical component 5.

PLT1: Japanese Patent Publication (A) No. 2005-83974

PLT2: Published Japanese Translation of PCT international Publication for Patent Application (Kohyo) No. 2009-506335

SUMMARY OF THE INVENTION

Technical Problem

In the above-mentioned phase shift amount measuring apparatus using the Mach-Zender interferometer, since the phase shift amount is calculated by the Fourier transform process on the basis of the phase shift method, high resolution measurement of the phase difference is achieved without the complicate calculation process. While, a beam splitter for dividing the transmitted beam through the sample into two beams is indispensable to the Mach-Zender interferometer. However, as the EUV radiation is absorbed by a glass substrate, the transflective type beam splitter in which a semitransparent film is formed on the glass substrate cannot be used in the EUVL. In this case, the use of a membranous beam splitter is supposed. But, the membranous beam splitter is difficult to maintain its surface precision and is subject to the external vibration, and thus the drawback arises that it is not applicable to the high resolution measurement of the phase difference. In addition, the Mach-Zender interferometer uses two wedge prisms, but it is difficult to construct the wedge prism by the optical material in which the EUV radiation is not absorbed. Therefore, because the wedge prism effectively operating in the EUV region is not present, it is difficult to construct the EUV phase shift amount measuring apparatus by use of the Mach-Zender interferometer.

As the interferometer other than the Mach-Zender interferometer, the Nomarski prism or Wollaston prism is known. In such prisms, the beam division is performed using the polarization action. However, since a suitable optical material in which the beam division in the EUV region is performed by the polarization action is not present, it is a fact that these prism cannot be used in the EUV region. Further, the Michelson interferometer or Linnik interferometer is also known. In these interferometers, the illumination beam is divided into two beams and the sample is disposed on the split path in order to perform the fringe-scan. However, if the sample being disposed on the split path, the propagating length of the divided beam is longer. In this case, the total path length of the interferometer varies more significantly by merely variation of the temperature of the optical system, and thus the drawback arises that the accuracy of the interferometer is susceptible to the influence of the environment temperature. Therefore, the above-mentioned interferometer is not suitable to the measurement of the big size sample such as the photomask.

In the above-mentioned interferometer using two diffraction grating, since the fringe-scan cannot be performed, the drawback arises that the arithmetic processing for calculating the phase shift amount is complicated. Especially, since the inverse diffraction theory is used to calculate the phase difference, the complicate calculation using a number of parameters is needed, and thus the problem arises of the large load being applied to the arithmetic processing. In addition, because the phase shift amount is calculated based on the inverse diffraction theory, the phase difference cannot be measured directly.

An object of the present invention is to realize an interferometer and a phase shift amount measuring apparatus which operate effectively in the EUV region.

Another object of the present invention is to realize an interferometer and a phase shift amount measuring apparatus in which the phase difference can be directly measured using the phase shift method (fringe-scan method).

Solution to Problem

The interferometer according to the invention comprising a illumination source for generating an illumination beam, an illumination system for projecting the illumination beam emitted from the illumination source onto a sample so as to illuminate two areas of the sample where are shifted from each other by a given distance, a detector for receiving radiation beams reflected by the two areas of the sample, and an imaging system for directing the radiation beams reflected by the two areas of the sample onto the detector, wherein said illumination system includes a first diffraction grating for diffracting the illumination beam emitted from the illumination source to produce a first and a second diffraction beams, wherein said two areas of the sample are illuminated by the first and second diffraction beams, respectively, and wherein said imaging system includes a second diffraction grating for diffracting the first and second diffraction beams reflected by the sample to produce a third and a fourth diffraction beams which are shifted from each other, and wherein an interference image consisting of the third and fourth diffraction beams is formed on the detector.

According to the invention, in the illumination system, there is arranged the first diffraction grating for producing at least two higher order diffraction beans from a single illumination beam in order to coherently illuminate two surface areas of the sample where are shifted from each other by a given distance. In addition, in the imaging system, there is arranged the second diffraction grating for producing at least two higher order diffraction beams to diffract the respectively reflected beams by the two surface areas of the sample and to produce the third and fourth diffraction beam which are shifted from each other by a given distance. On the detector, two diffraction images which are partially overlapped each other are formed by the third and fourth diffraction beams. Since the third and fourth diffraction beams emitted from the second grating include a phase difference information corresponding to a path-length difference between the two paths which respectively pass through the two different points of the sample, the interference image including the phase difference caused by the structural difference of the sample surface is formed on the detector. As the result of this, the interferometer of the invention constructs a two beams interferometer so that refined structural changes of the sample surface can be detected as the interference image. That is, various characteristics of the sample can be analyzed by processing the luminance signal outputted from the detector. As one example, it is possible to measure the phase shift amount and the absorption of the absorber pattern formed on the EUV mask used for the EUVL by using the phase shift method based on the fringe-scan. Of course, since the luminance value of the interference image includes the height information of the sample surface, the interferometer according to the invention is applicable to the measurement of the shape or deviation of the sample surface. More important, since all of the optical elements arranged between the illumination source and the detector can be constructed by the reflective elements, an interferometer preciously operating in the EUV region can be realized. Furthermore, in the present specification and claims, the wordings of "radiation beam" and "illumination beam" mean infrared light, visible light, ultraviolet light and X ray. In addition, the wording of "radiation source" and "illumination source" mean a radiation source for generating X ray beam and a light source for generating ultraviolet beam, visible beam and infrared beam.

In a preferable embodiment of the interferometer according to the invention, the first and second diffraction beams illuminate the two areas of the sample coherently, and the third and fourth diffracted beams are partially overlapped with each other on the detector. The first and second diffraction beams for illuminating the two surface areas of the sample emanate from the same illumination source. Therefore, the two surface areas of the sample can be illuminated coherently regardless of the characteristics of the illumination source. As the result of this, it is possible to use a $Sn^+$ plasma source which has been used as the practical exposure source of the EUVL as the illumination source.

In a preferable embodiment of the interferometer, the first and second diffraction gratings comprise a phase diffraction grating for producing at least two higher order diffraction beams. According to the inventor' various analysis results for the phase diffraction grating, it has been found that at least two higher order diffraction beams can be generated from the radiation beam of a single wavelength, if the diffraction grating is designed based on the grating pattern defined by two spatial frequency components. As one example, the diffraction grating for generating at least two higher order diffraction beams at different diffraction angles can be realized, when the depth of the grating groove is set to $\lambda/4$ ($\lambda$ is the wavelength of the illumination beam), the least common multiple of the periods of the two spatial frequency is assumed as the basic period of the diffraction grating, and the grating pitch is designed by the logical sum, logical product or exclusive OR of the periods of the two frequency components. Therefore, the two surface areas of the sample where are laterally shifted from each other by the given distance can be coherently illuminated by disposing the two frequency diffraction grating whose grating pattern is designed based on the two frequency components in the illumination system. In addition, if the diffraction grating having the same structure being arranged in the illumination system and the imaging system, respectively, two diffraction images which are laterally shifted from each other by the given distance are formed from the two reflected beams by the two surface areas of the sample, and thus an interference image consisting of two diffraction images is formed on the detector. In the two frequency diffraction grating whose grating pitch is designed by two spatial frequency components, the shifted distance between the two higher order diffraction beams can be arbitrarily set, the interferometer according to the invention is preferable to the interference measurement needing relatively large shifted distance such as a differential interferometry.

In a preferable embodiment of the interferometer, the first and second diffraction gratings comprise a grating having the same structure, and the first diffraction grating is arranged at the pupil position or the neighborhood of the illumination system, and the second diffraction grating is arranged at the pupil position or the neighborhood of the imaging system. If the first and second diffraction gratings having the same structure and being arranged at the conjugate position with each other, the first diffraction grating disposed in the illumination system operates as a two beams producing element, and the second diffraction grating disposed in the imaging system operates as a beam combining element for combining the two reflected beams by the two areas of the sample so as to form the interference image consisting of the two reflected beams. Thereby, a two beam interferometer can be realized.

In a preferable embodiment of the interferometer, an objective system is arranged in the paths between the sample and the first and second diffraction gratings, and the first and second diffraction beams emitted from the first diffraction grating are directed onto the sample through the objective system, and the first and second diffraction beams emitted from the sample are directed onto the second diffraction grating through the objective system. Further, in this embodiment, the objective system comprises a plane mirror and two concave mirrors, and its focus point is set at infinity, and one half area of the objective system forms a part of the illumination system and the remaining half area forms a part of the imaging system. As to the objective system, since the objective system whose focus point is set at infinity is constructed by combining the plane mirror and concave mirror, the pupil positions of the illumination system and imaging system are formed outside of the objective system. As the result of this, the first and second diffraction gratings are arranged at the pupil position, respectively. Therefore, it becomes possible to locate the first and second diffraction gratings at the conjugate position with each other.

The phase shift amount measuring apparatus according to the invention comprises;

an illumination source for generating an illumination beam;

an illumination system for projecting the illumination beam emitted from the illumination source onto the photomask so as to illuminate two areas of the photomask where are shifted from each other by a given shearing distance;

a detector for receiving radiation beams emitted from the two areas of the photomask;

an imaging system for directing the radiation beams reflected by the two areas of the mask onto the detector;

a stage supporting the photomask and comprising an X-Y moving mechanism and a tilting mechanism for tilting the mask; and a processor coupled to the detector to calculate the phase shift amount of the phase shifter; wherein said illumination system includes a first diffraction grating for diffracting the illumination beam emitted from the illumination source to produce a first and a second diffraction beams, wherein said two areas of the photomask are illuminated by the first and second diffraction beams, respectively, and wherein said imaging system includes a second diffraction grating for diffracting the first and second diffraction beams emitted from the photomask to produce a third and a fourth diffraction beams which are shifted from each other, and wherein an interference image consisting of the third and fourth diffraction beams is formed on the detector, and wherein a fringe-scan process for the first and second diffraction beams is performed by scanning the inclined angle of the photomask using the tilting mechanism of the stage, and wherein the processor calculates the phase shift amount using the output signal supplied from the detector and the fringe-scan information of the tilting mechanism.

In the phase shift amount measuring apparatus of the invention, the fringe-scan is carried out by tilting the stage while the optical system is maintained in the fixed condition, and therefore the advantageous effect is achieved that the stable fringe-scan can be performed without exerting adverse influences on the optical system.

The phase shift amount measuring apparatus according to the invention comprises;

an X-ray source for generating an illumination beam of EUV region;

an illumination system for projecting the illumination beam emitted from the X-ray source onto the photomask so as to illuminate two areas of the photomask where are shifted from each other by a given shearing distance;

a detector for receiving reflected beams by the two areas of the photomask;

and an imaging system for directing the reflected beams by the two areas of the photomask onto the detector;

a stage supporting the photomask and comprising an X-Y moving mechanism and a tilting mechanism for tilting the photomask; and a processor coupled to the detector to calculate the phase shift amount of the absorber pattern; wherein said illumination system includes a first diffraction grating for diffracting the illumination beam emitted from the X-ray source to produce a first and a second diffraction beams, wherein said two areas of the photomask are illuminated by the first and second diffraction beams, respectively, and wherein said imaging system includes a second diffraction grating for diffracting the first and second diffraction beams reflected by the photomask to produce a third and a fourth diffraction beams which are shifted from each other, and wherein an interference image consisting of the third and fourth diffraction beams is formed on the detector, and wherein a fringe-scan process for the first and second diffraction beams is performed by scanning the inclined angle of the photomask using the tilting mechanism of the stage, and wherein the processor calculates the phase shift amount of the absorber pattern using the output signal supplied from the detector and the fringe-scan information of the tilting mechanism.

In a preferable embodiment of the phase shift amount measuring apparatus of the invention, a $Sn^+$ plasma source for producing an EUV beam whose emission peak wavelength is 13.5 nm is used as the EUV source, and a diffraction grating operating as a spectroscope and a field stop are arranged between the $Sn^+$ plasma source and the first diffraction grating. The $Sn^+$ plasma source is an exposure source which has been practically used in the EUVL. However, the $Sn^+$ plasma source includes the problem that its emission spectrum is relative broad. In order to solve such problem, according to the invention, the diffraction grating operating as the spectroscope and the field stop are arranged between the $Sn^+$ plasma source and the first diffraction grating. In this case, since the EUV radiation whose wavelength is shifted from the 13.5 nm is cut by the field stop, the phase shift amount can be measured by only use of the EUV beam of the single wavelength of 13.5 nm. As the result of this, it is possible that the phase shift amount of the absorber pattern formed on the EUV mask can be measured by the same condition as the practical EUVL.

Advantageous Effects of Invention

According to the present invention, the interferometer and the phase shift amount measuring apparatus operating in the EUV region can be realized, because a fine height variation of the sample surface can be measured as the phase difference and all of the optical elements arranged on the path between the illumination source and the detector are constructed by the optical element of reflection type. Further, since the fringe-scan is performed by tilting the stage for supporting the sample, the phase difference between the two surface areas of the sample can be obtained by use of the phase shift method, and thereby it becomes possible to preciously measure the phase shift amount without increasing the processing load of the processor.

DESCRIPTION OF THE EXEMPLARY EMBODIMENTS

Figure 1A:
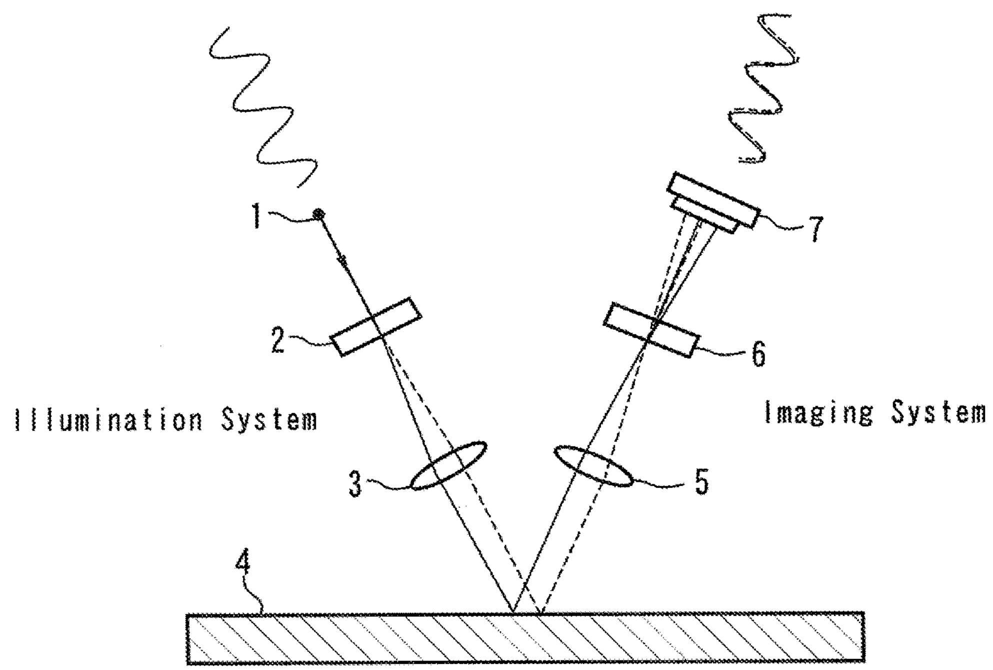
FIGS. 1A and 1B are views showing a basic principle of the interferometer according to the invention.

FIG. 1 shows the basic principle of the interferometer according to the invention, FIG. 2 shows the diffraction characteristic of the diffraction grating of two frequency type used in the interferometer of the invention, and FIG. 3 shows phase variation caused by the fringe-scan. Referring to FIG. 1, an illumination source 1 operates as a micro illumination source and produces an illumination beam having a single wavelength. The illumination beam is directed onto a first diffraction grating 2. The first diffraction grating 2 includes a grating pattern defined by two spatial frequency components and is comprised of a diffraction grating of two frequency type for generating at least two higher order diffracted beams. As one example, such diffraction grating of two frequencies type generates a zero-th beam, ±20-th diffracted beams and ±21-th diffracted beams by designing the grating pattern based on the logical sum of two spatial frequency components. According to the present embodiment, among the five beams, the +20-th and +21-th diffracted beams are used as a first and second diffraction beams which illuminate two different surface areas of a sample, respectively. Furthermore, in order to clarify the drawings, in FIG. 1 and FIG. 3, only the first and second diffraction beams are illustrated and other diffraction beams are omitted. The first diffraction beam (+20-th diffracted beam) is illustrated by a solid line and the second diffraction beam (+21-th diffracted beam) is illustrated by a broken line. The first and second diffraction beams emanate from the first diffraction grating 2 at different diffraction angles each other, propagate along the different paths, respectively, and are made incident upon the sample 4 through a condenser lens 3 to coherently illuminate two surface areas of the sample which are laterally shifted from each other by a predetermined distance. Since the first and second diffraction beams emanate from the same illumination source, the two surface areas of the sample are illuminated coherently. Furthermore, the distance between the two illuminated areas on the sample is a shearing amount of the interferometer. The two diffraction beams reflected by two illumination areas of the sample are focused by the objective system 5 and are directed onto a second diffraction grating 6.

In the present example, the second diffraction grating 6 is comprised of the diffraction grating of two frequency components type having the same structure as the first grating and is located at a conjugate position with the first diffraction grating 2. That is, the paths from the illuminated points on the sample to the first grating 2 of the illumination system and to the second grating 6 of the imaging system are formed symmetrically each other. Therefore, the second grating 6 further diffracts the incident first and second diffraction beams reflected by the sample to produce the zero-th beam, ±20-th diffraction beams and ±21-th diffraction beams for each first and second diffraction beams. These diffraction beams emanate from the second grating 6 at different diffraction angles, respectively. According to the present embodiment, among the diffraction beams emitted from the second diffraction grating, only the +20-th and +21-th diffracted beams are used for the measurement as a third and a fourth diffraction beams. That is, the first and second diffraction beams reflected by the sample are further diffracted by the second grating 6 so as to form the third and fourth diffraction beams which are laterally shifted from each other by the predetermined distance (shearing distance). These diffracted beams are made incident on a detector 7. Therefore, on the detector 7, there are formed two diffraction images which are laterally shifted by the predetermined distance. Since the third and fourth diffraction beams incident on the detector 7 emanate from the same radiation source, these diffraction beams are interfered mutually. Therefore, on the detector, there is formed an interference image which corresponds to the path length difference between two diffraction beams. In this way, the interferometer according to the invention constructs a two-beams interferometer. Furthermore, in FIGS. 1 and 3, upward of the detector 7, there are illustrated the phase waveforms of the third and fourth diffraction beams by a solid line and a dot line.

Figure 1B:
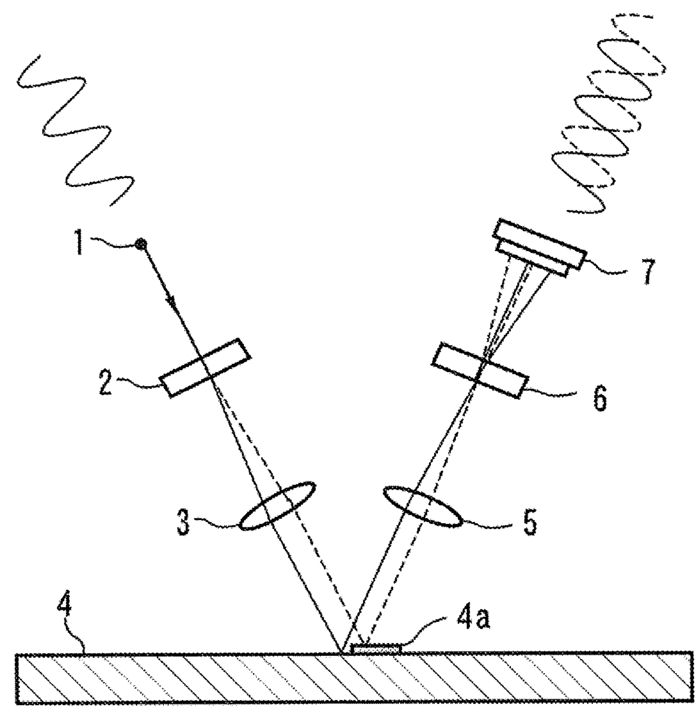

In the present example, as the sample 4 to be measured, a photomask used in the EUVL (EUV mask) is used. The photomask used in the EUVL comprises a reflection film formed on a substrate and absorber patterns formed on the reflection film and functioning as a shielding pattern. Such absorber pattern is designed so that its thickness corresponds to $\lambda/4$. The $\lambda$ is an exposure wavelength of the EUVL which is 13.5 nm. FIG. 1A illustrates the state in which the sample surface is plane, namely two diffraction beams are made incident upon the reflection film, and FIG. 1B illustrates the state in which the first diffraction beam strikes the reflection film and the second beam strikes the absorber pattern 4*a*.

When both of the first and second diffraction beams are made incident on the reflection film, the path lengths of the first and second diffraction beams are equal to each other. Therefore, as shown in FIG. 1A, the interference image having the same phase state are formed on the detector, because the third and fourth diffraction beams are in phase and thereby the combined beam consisting of the third and fourth diffraction beams has no phase difference caused by the sample surface. On the contrary, as shown in FIG. 1B, when the first diffraction beam illuminates the reflection film and the second beam illuminates the absorber pattern, between the third and fourth diffraction beams there is introduced the path length difference which is substantially two times as large as the thickness of the absorber pattern. As the result of this, the phase difference corresponding to the double thickness of the absorber pattern is introduced between the third and fourth diffraction beams, and thereby as shown in the phase waveform illustrated in FIG. 1B, the interference image having the luminance value corresponding to the phase difference between the two diffraction beams is formed on the detector. Therefore, by comparing the phase states of the two interference images formed on the detector with each other, the variation in height of the sample surface can be detected as the phase difference. That is, by comparing the phase states of the interference images formed by the reflected beams by the absorber pattern and by the reflection film, respectively and formed by the two reflected beams by the reflection film with each other, the phase shift amount of the absorber pattern relative to the reflection film can be detected as the phase difference. In addition, the thickness of the absorber pattern and the variant in height of the sample surface can be measured using the detected phase shift amount.

According to the invention, the phase comparison for two interference images is performed by the fringe scan process. In the present embodiment, the fringe-scan is performed by tilting the stage on which the sample is supported so as to incline the sample surface with respect to the incident beams. By tilting the sample surface, the path length of the diffraction beam which is reflected by the sample surface and directed onto the detector is varied, and thereby the phase modulation process can be carried out. That is, by tilting the sample surface, the path length of the diffraction beam incident upon the detector is varied in accordance with the inclined angle of the sample surface. Therefore, by continuously scanning the inclined angle of the stage, the phase modulation data can be obtained, and thereby phase comparison can be performed. For example, the absorber pattern is designed so as to introduce the phase difference of $\lambda/2$ between the reflected beams by the reflection film and by the absorber pattern. Therefore, when the first and second diffraction beams respectively illuminate the reflection film and the absorber pattern, there is formed the interference image including the phase difference of $\lambda/2$ as the basis of the interference image formed when both of the first and second beams illuminate the reflection film. In addition, if the stage is continuously inclined, the apparent path lengths of the first and second diffraction beams are varied and the path length difference corresponding to the inclined angle is introduced between the reflected first and second diffraction beams. Therefore, the phase shift amount of the absorber pattern can be detected by continuously tilting the stage to introduce the phase modulation of one period between the first and second diffraction beams. That is, the phase shift amount of the absorber pattern can be detected by comparing the phase states of the two interference images with each other by use of the scanning of the inclined angle of the stage.

Figure 2A:
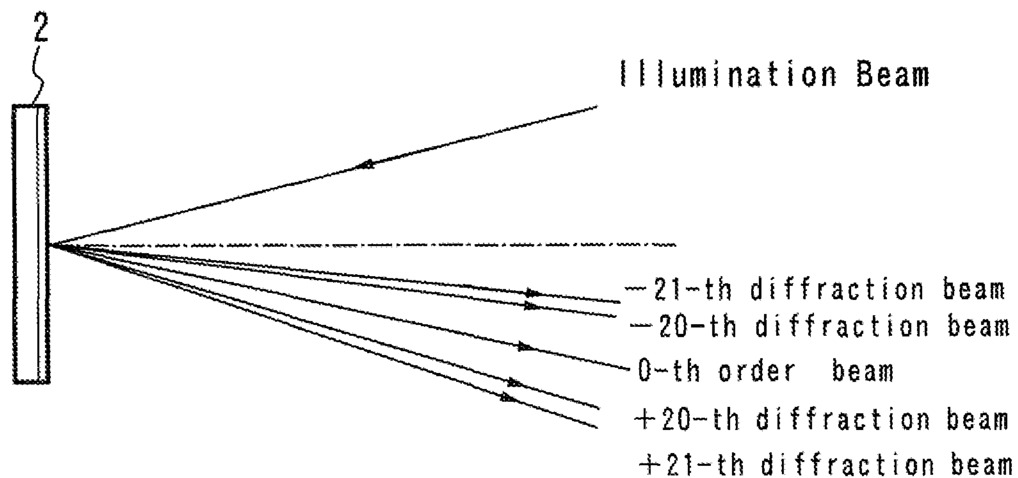
FIGS. 2A and 2B are views showing the diffraction characteristic of the diffraction grating of two frequency type used in the interferometer and the phase shift amount measuring apparatus of the invention.
Figure 2B:
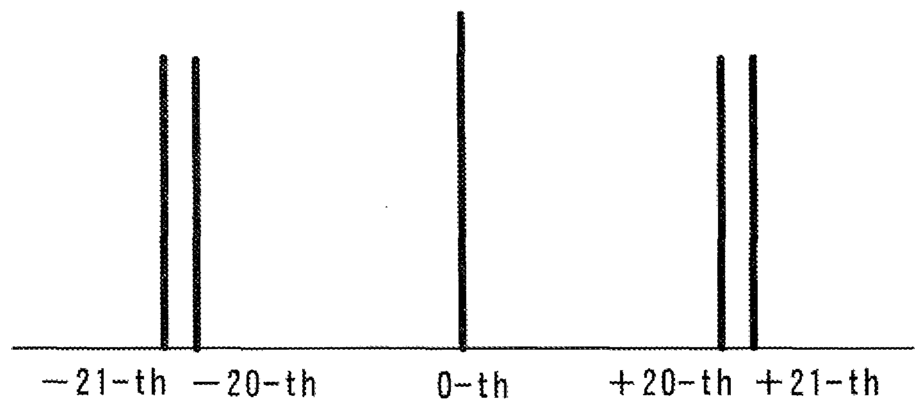

FIG. 2 is a view showing the diffraction characteristic of the first diffraction grating arranged in the illumination system. In the present example, as the first and second grating, the phase grating of two frequency components type including the grating pattern defined by two frequency components is used. The depth of the grating groove of such diffraction grating is set to $\lambda/4$. FIG. 2A shows the diffraction characteristic of the first diffraction grating arranged in the illumination system and FIG. 2B shows the relation between the diffraction angle and the intensity of the diffraction beam. In the example, the phase diffraction grating of reflection type which is designed to produce the zero-th beam, ±20-th diffraction beams and ±21-th diffraction beams will be explained. When the illumination beam emitted from the illumination source is made incident upon the first grating, the first grating generates the zero-th beam, ±20-th and ±21-th diffraction beams. Among five beams, higher order diffraction beams of the +20-th and +21-th are used as the first and second illumination beams for coherently illuminating two points on the sample which are laterally shifted from each other by the predetermined distance. In this case, since the +20-th and +21-th diffraction beams emanate at sufficiently large diffraction angle from the zero-th beam, it is possible to locate the illuminated areas of the zero-th, −20-th and −21-th beams out of the field of view of the imaging device by positioning the illuminated areas of the +20-th and +21-th diffracted beams at the center of the field of view.

Five reflected beams by the sample are directed onto the second grating. The second grating has the same structure as the first grating and is disposed at the conjugate position with the first grating. These five reflection beams are diffracted by the second grating to produce the zero-th beam, ±20-th diffraction beams and ±21-th diffraction beams for each reflection beams. Among these diffraction beams, the +20-th and +21-th diffraction beams are used as the third and fourth diffraction beams for the measurement, and are directed onto the detector. Since the first and second diffraction beams are coherent each other, the third and fourth diffraction beams are also coherent each other. Therefore, on the detector, there is formed the interference image consisting of the third and fourth diffraction beams and including the phase difference caused by the sample surface.

Figure 3A:
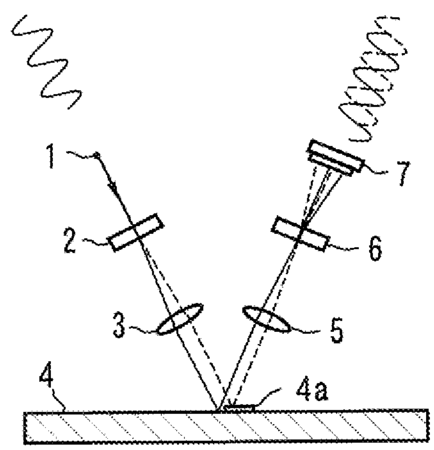
FIGS. 3A, 3B and 3C are views showing a fashion of the fringe scanning according to the invention.
Figure 3B:
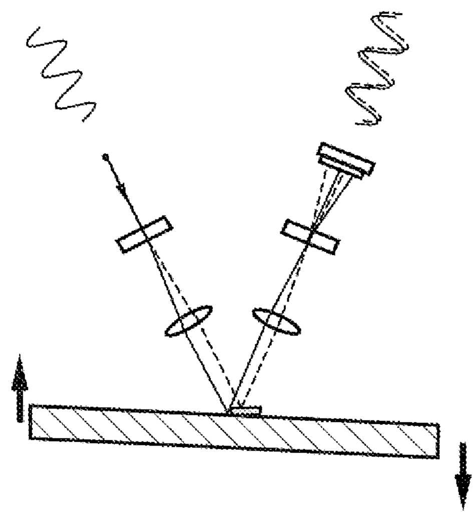
Figure 3C:
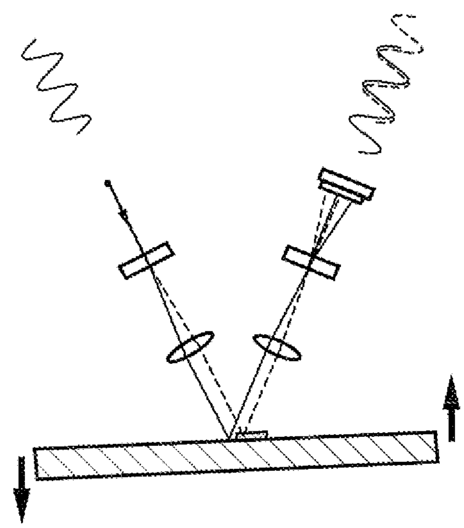

FIG. 3 is a view for explanation of the fringe-scan method according to the invention. In the present example, the fringe-scan is performed by using a tilting mechanism of the stage which holds the sample. For example, a reference position of the fringe-scan is set to a horizontal position of the stage. It is possible to introduce the phase difference of one period between the first diffraction beam (the first illumination beam) and second diffraction beam (the second illumination beam) by inclining the stage from the reference position. FIG. 3A denotes the state in which the stage is positioned at the reference position. In this state, the first diffraction beam illuminates the reflection film and the second diffraction beam illuminates the absorber pattern. Therefore, as shown in the phase waveform illustrated upward the detector 7 in FIG. 3A, the phase difference of $\lambda/2$ is formed between the third diffraction beam and the fourth diffraction beam. FIG. 3B denotes the state in which the stage is inclined toward the right side so that the phase modulation of $+\lambda/2$ is introduced, and FIG. 3C denotes the state in which the stage is inclined toward the left side so that the phase modulation of $-\lambda/2$ is introduced. In this way, it is possible to perform the phase modulation of one period for the first and second diffraction beams by continuously inclining the stage in the shearing direction. In the fringe-scan according to the invention, only the stage and the sample are tilted while the optical system is held in stationary state, and thereby it is possible to perform the stable fringe-scanning or the stable phase comparison process.

Figure 4:
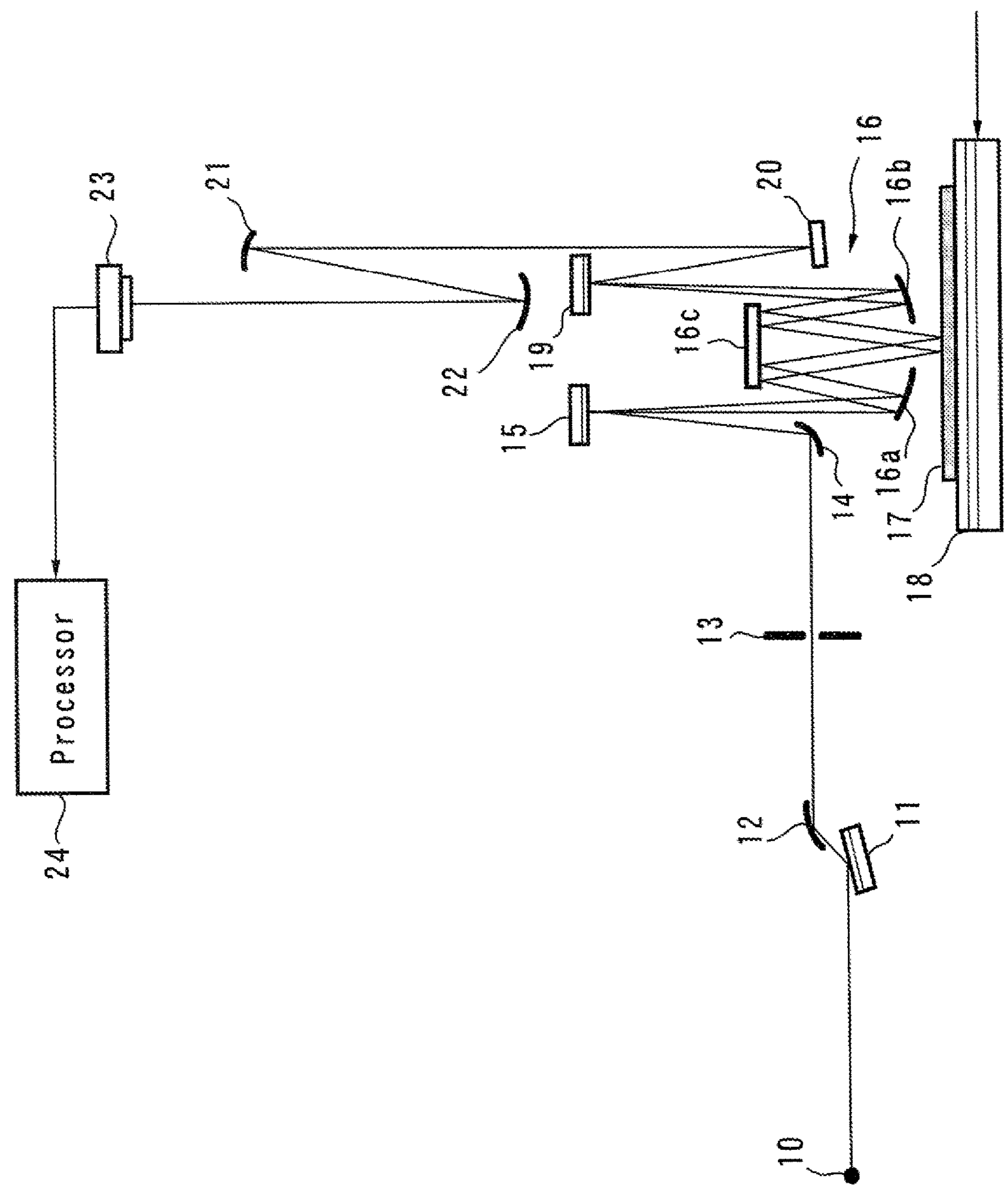
FIG. 4 is a view showing a specific example of the interferometer and the phase shift amount measuring apparatus according to the invention.
Figure 5:
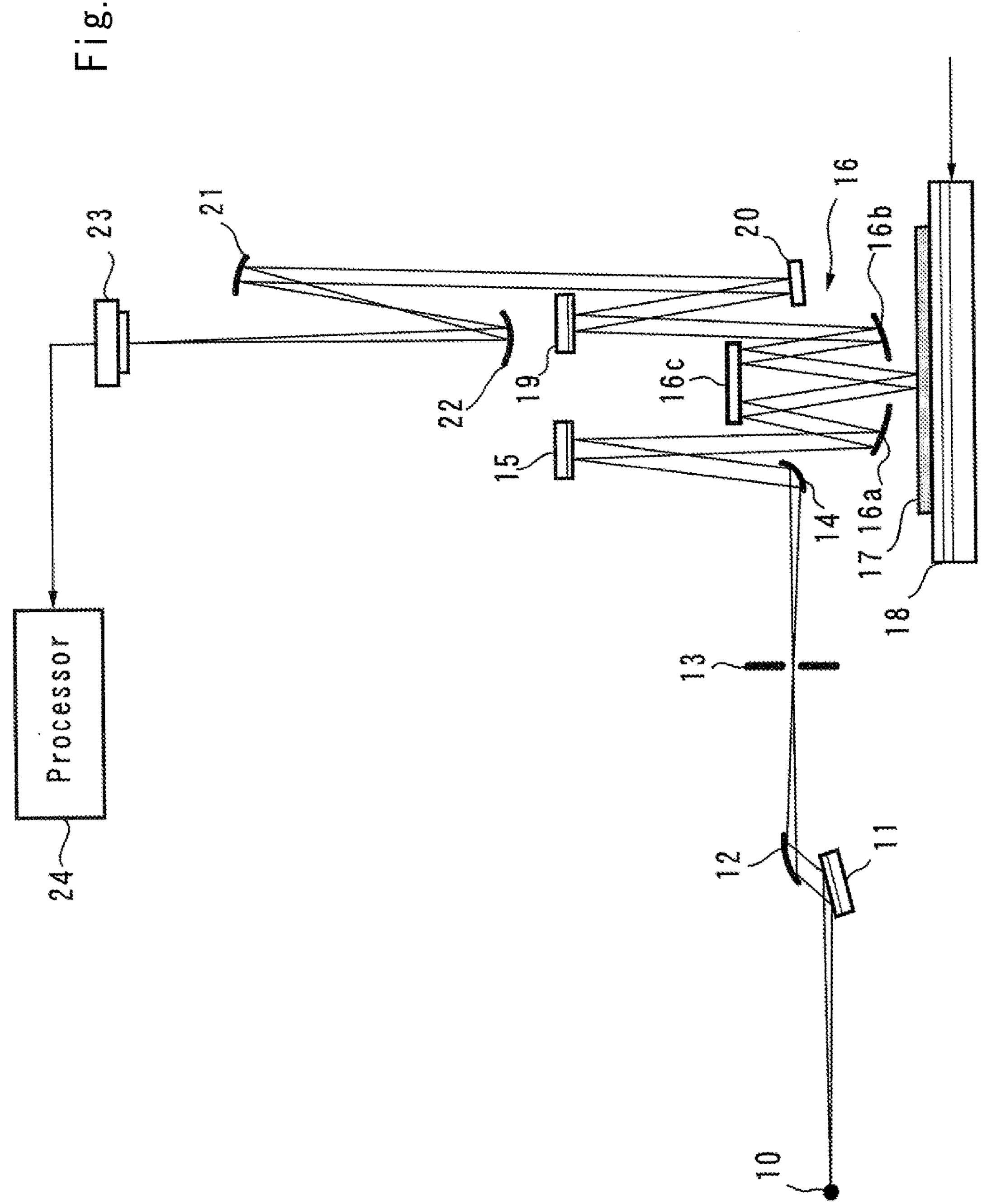
FIG. 5 is a view showing a specific example of the interferometer and the phase shift amount measuring apparatus according to the invention.

FIG. 4 and FIG. 5 illustrate a concrete embodiment of the interferometer and the phase shift amount measuring apparatus according to the invention. FIG. 4 illustrates a principal ray viewed from the imaging device, and FIG. 5 illustrates homologous rays. In the present example, the interferometer and the phase shift amount measuring apparatus for measuring the phase shift amount of the absorber pattern formed on the reflection film of the photomask used in the EUVL (EUV mask) will be explained. Of course, the interferometer of the invention can also operate in the wavelength range of ultraviolet, visible and infrared regions. Further, the present invention is applicable to measure the phase shift amount of a half-tone film of the photomask of transmission type and the phase difference of various optical elements or optical thin films. Further, the present invention is applicable to measure the shape or distribution in height of the sample surface.

An illumination source 10 produces an illumination beam. In the present embodiment, as the illumination source (EUV source), for example a $Sn^+$ plasma source is used. The $Sn^+$ plasma source produces an EUV beam whose wavelength is 13.5 nm and has been practically used as the EUV exposure source of the EUVL. Therefore, the practical phase shift amount of the absorber pattern used in the EUVL can be just measured. Furthermore, another X-ray source such as a Xenon plasma source, a femtosecond laser harmonic source and a synchrotron can be used. Further, in the present invention, the radiation sources for producing a coherent beam or an incoherent beam can be used. Further, the present invention is applicable to an interferometer operating in a DUV region or infrared region. In this case, a light source for producing DUV light or infrared light is used.

The illumination beam emitted from the illumination source 10 is directed onto a first diffraction grating 11. The first grating 11 is a grating of reflection type which operates as a spectroscope. The $Sn^+$ plasma source has relatively broad emission spectrum. When the $Sn^+$ plasma source is used as the illumination source, a diffraction angle of the radiation beam may be spread and thereby an image of a sample formed on a detector may be blurred under the influence of a chromatic aberration. In order to overcome such problem, in the present example, only a EUV radiation beam having a peak emission wavelength is used as the illumination beam by providing the diffraction grating 11 operating as the spectroscope. In this case, it is possible to project only the EUV radiation having the peak emission wavelength of 13.5 nm onto the EUV mask by providing a field stop in the later passage. The area where is illuminated by the EUV radiation having the emission peak wavelength is viewed as belt-shape, and thus it is possible to perform the measurement with the EUV radiation whose wavelength is 13.5 nm by positioning a measuring point at the center of the belt-shape area.

The radiation beam emitted from the first diffraction grating 11 is reflected by an off-axis ellipsoidal mirror 12 and passes through a field stop 13 arranged at an intermediate image point. The field stop 13 has a rectangular opening and defines an illumination area on the sample. By providing the field stop, it is possible to use only the EUV radiation having the emission peak wavelength of 13.5 nm as the illumination beam. The radiation beam passing through the field stop 13 is made incident upon an aspheric concave mirror 14. The off-axis ellipsoidal mirror 12 and aspheric concave mirror 14 are comprised of a reflection mirror having a multi-layer structure in which silicon layers and molybdenum layers are stacked alternately. The radiation beam is converted into a parallel beam by the aspheric concave mirror 14 and strikes a second diffraction grating 15 which is arranged at a pupil position of the illumination system, namely at a pupil position of an objective system. This second diffraction grating 15 corresponds to the first diffraction grating explained in FIG. 1.

The second diffraction grating 15 is constructed by a two frequencies phase grating of reflection type for producing a zero-th beam, ±20-th and ±21-th diffracted beams. In the present example, the +20-th and +21-th diffracted beams are used as a first and second diffraction beams (illumination beams). These first and second diffraction beams respectively illuminate two surface areas of the photomask coherently.

The illumination beams emitted from the second diffraction grating 15 strike the objective system 16. In the present embodiment, the objective system whose focus point is set at infinity is used. The objective system 16 comprises two aspheric concave mirrors 16*a* and 16*b* and a plane mirror 16*c*. One half area (left side half in FIGS. 4 and 5) of the objective system forms a part of the illumination system and the remaining half area (right side half in FIGS. 4 and 5) forms a part of an imaging system. Furthermore, two aspheric concave mirrors can be constructed by a single aspheric concave mirror having an opening at its center. The illumination beams emitted from the second grating 15 are reflected by the concave mirror 16*a* and the plane mirror 16*c*, respectively and strike the photomask 17 which is used for the EUVL. The incident angle of the illumination beam with respect to the photomask is set at 6°. If the incident angle being set at 6°, it is possible to illuminate the photomask at the same illumination angle as the practical exposure angle of the EUVL.

The photomask 17 comprises a substrate, a reflection film of a multi-layer structure consisting of silicon layers and molybdenum layers which are stacked alternately on the substrate and absorber patterns formed on the reflection film. The absorber pattern functions as a shielding pattern and also functions as a phase shifter introducing a phase difference of λ/2 between the reflected radiations by the reflection film and by the absorber pattern. A monitor pattern consisting of the absorber is formed out of a pattern forming region of the photomask 17, and in the present example, the phase shift amount of the monitor pattern is measured. Such monitor pattern is formed in a pattern forming process together with the absorber patterns in the pattern forming region, and thus the phase shift amount of the absorber pattern formed in the pattern forming region can be detected by measuring that of the monitor pattern. In this embodiment, as the monitor pattern, an absorber having a rectangular area of 4 μm×4 μm is used. The size and shape of the monitor pattern can be suitably adjusted based on a characteristic of the photomask and the measuring object, and for example the monitor pattern having a strip shape can be used.

In the present example, the displacement amount or the shift amount between the first and second diffraction beams on the photomask is set to be 5 μm, and thus the monitor pattern and the adjacent area of the reflection film are illuminated coherently by two diffraction beams which are shifted from each other by 5 μm. Such shift amount can be selected freely on the basis of the design value of the grating pattern of the second grating. The shift amount of 5 μm is one example and can be suitably set based on the sample to be measured and the measurement object. According to the invention, two reflected beams which are respectively reflected by two different surface areas of the photomask are combined by the imaging system in order to form an interference image on the detector. Then, the phase shift amount and the transmittance of the absorber pattern are measured based on the interference image consisting of the reflected beams by the monitor pattern and by the reflection film using the fringe-scan method.

The EUV mask 17 is held on a mask-stage 18. The mask-stage 18 comprises a stage for holding the photomask, an X-Y moving mechanism and a tilting mechanism (tilting stage). The operator can locate the image of the monitor pattern at the center of the field of view of the imaging device using the X-Y moving mechanism. The tilting mechanism is constructed so as to incline the stage in the diffraction direction of the second diffraction grating, and the fringe-scan is performed by scanning the inclined angle of the stage. That is, the fringe-scan is performed in such a manner that a path length difference of one period is introduced between two incident diffraction beams by continuously changing the inclined angle of the stage in the diffraction direction from the reference position. The mask-stage 18 is controlled by a driving signal supplied from a processor. The inclined angle, namely the introduced path length difference corresponding to the phase modulation amount is controlled by the processor.

The first and second diffraction beams respectively reflected by the two illuminated areas on the photomask 17 are made incident upon the objective system 16. These reflected beams are reflected by the plane mirror 16*c* and the concave mirror 16*b*, respectively and strikes the third diffraction grating 19. The third grating 19 comprises the two frequencies type phase grating of reflection type having the same construction as the second grating 15 and is arranged at the pupil position of the imaging system or the neighborhood, namely at the conjugate position with the second grating 15. This third grating corresponds to the second grating explained in FIG. 1 and further diffracts the incident first and second diffraction beams to produce the zero-th beam, ±20-th and ±21-th diffraction beams, respectively. In the example, among the five diffracted beams emitted from the third grating 19, the +20-th and +21-th diffraction beams are used for the measurement as a third and a fourth diffraction beams. The diffraction beams emitted from the third grating 19 are reflected by a plane mirror 20 and two aspheric concave mirrors 21 and 22, and is directed onto the detector 23. On the detector, two diffraction images are formed by the third and fourth diffraction beams, respectively. These diffraction images are laterally shifted from each other by a predetermined distance corresponding to the shearing amount of the third grating and are partially overlapped each other. Therefore, on the detector, there is formed an interference image consisting of the two diffraction images which are formed by the third and fourth diffraction beams, respectively. As the detector 23, a two dimensional imaging device having a plurality of radiation-sensitive elements which have sensitivity in the EUV range and are arranged in the two dimensional array can be used, and for example a BT-CCD is preferable.

The image signal outputted from the imaging device 23 is supplied to the signal processor 24. The signal processor 24 calculates and produces the phase shift amount of the monitor pattern based on the phase shift method using the fringe-scan signal supplied from the tilting mechanism of the stage and the image signal supplied from the imaging device.

According to the apparatus shown in FIG. 4 and FIG. 5, the elements arranged in the path between the illumination source and the detector are constructed by the reflection mirrors and diffraction gratings of reflection type, and thereby the interferometer and the phase shift amount measuring system operating in the EUV region stably can be realized.

A method for designing the structure of the second phase diffraction grating of reflection type provided in the illumination system will be explained. In the present example, the third grating arranged in the imaging system is comprised of the grating having the same structure as the second grating. The grating pattern of the second grating is formed based on the logical sum of two spatial frequency components. That is, the grating pattern of the second grating is formed based on a composite waveform defined by the logical sum of two square waves having the different spatial frequency each other. In this case, the second diffraction grating produces five diffraction beams of a zero-th beam and higher order diffracted beams of a first and second beams in the +side and −side in total. According to the present embodiment, the first and second higher order diffracted beams in +side are used as the illumination beams. Here, the grating pattern can be also formed based on the logical product. Because, the grating pattern defined by the logical product is same as the grating pattern which is obtained by inverting the pattern formed by the logical sum.

Figure 6A:
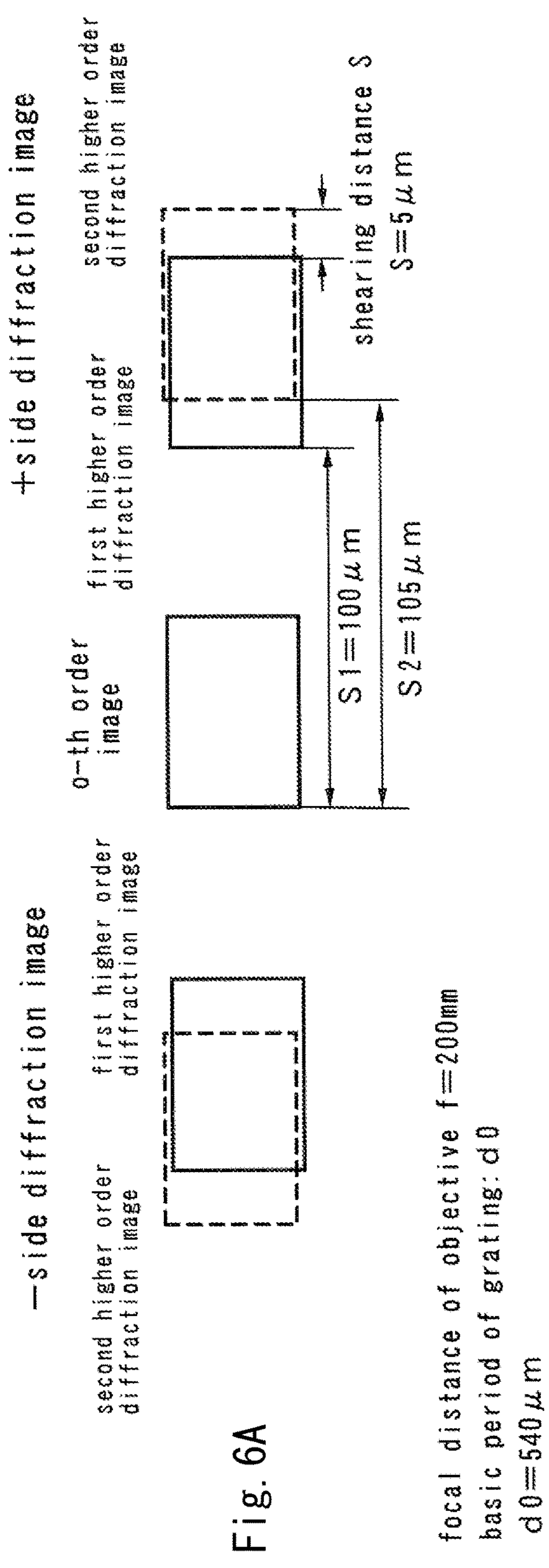
FIGS. 6A and 6B are views showing design data which are used for the structural design of the diffraction grating of two frequency type.

FIG. 6 denotes the design data which are used for the structure design of the phase diffraction grating of two frequencies type as one example. FIG. 6A illustrates a positional relation between a zero-th order diffraction image and two higher order diffraction images formed on the sample by the zero-th beam, first and second diffraction beams, respectively. As the design data, the shifted distances S1 and S2 from the zero-th image to each of the first and second higher order diffraction images are set such that S1 and S2 are equal to 100 μm and 105 μm, respectively. Therefore, the first and second higher order diffraction images are formed at the positions where are 100 μm and 105 μm away from the zero-th image, respectively. Then, the displacement amount S between the first diffraction image and the second diffraction image is the shearing amount and is set to 5 μm. And further, the focal length f of the objective system is 200 mm, and the field size is 80 μm. The wavelength of the illumination beam λ is 13.5 nm.

The basic period $d_0$ of the grating is defined by the following equation.

$$d_0 = f \times \lambda / S = 540\ \mu m$$

The pitch $d_1$ of the first spatial frequency is defined by the following equation using young's formula.

$$d_1 \times \sin\theta = \lambda$$

$$d_1 = \lambda \times (f/S1) = 27\ \mu m$$

The pitch $d_2$ of the second spatial frequency is defined by the following equation.

$$d_2 \times \sin\theta = \lambda$$

$$d_2 = \lambda \times (f/S2) = 27.714\ \mu m$$

Here, a least common multiple of the periods of the two spatial frequency components is regarded as the basic period of the diffraction grating. Therefore, the number of the periods P1 and P2 of the first and second spatial frequency components included in one basic period are as follows.

$$P1 = 540\ \mu m/27\ \mu m = 20\ \text{periods}$$

$$P2 = 540\ \mu m/27.714\ \mu m = 21\ \text{periods}$$

Therefore, the diffraction beams formed by the first and second spatial frequency components emanate from the grating as the 20-th and 21-th diffracted beams, respectively. As the result of this, the phase diffraction grating of two frequencies type produces five diffraction beams of zero-th beam, ±20-th beams and ±21-th beams in total.

Figure 6B:
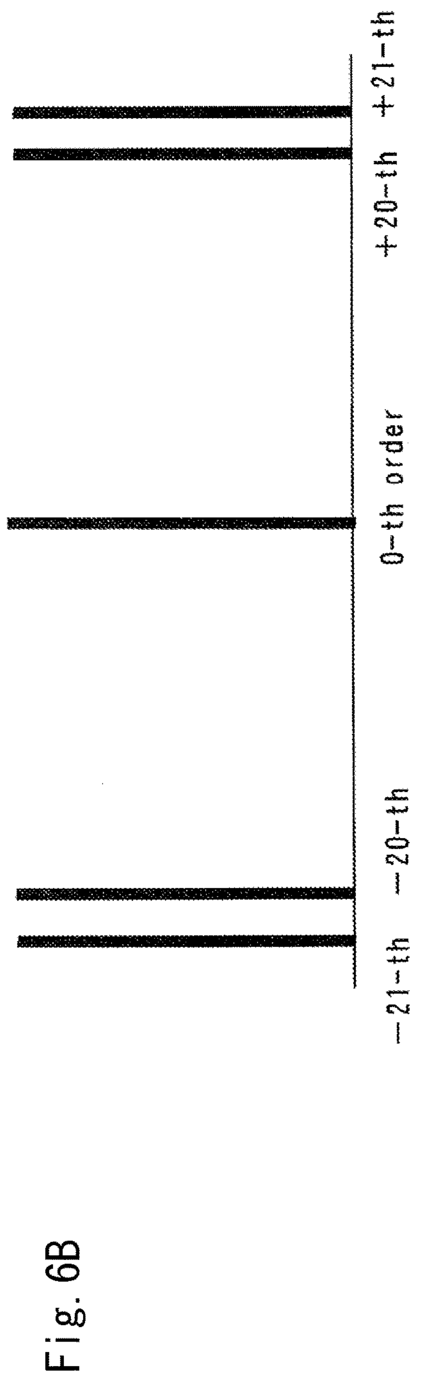

FIG. 6B denotes the simulation result for the relation between the diffraction angle and the intensity of the diffraction beam. The horizontal axis denotes the position in the diffraction angle direction and the vertical axis denotes the intensity of the diffraction beam. The zero-th beam is emitted from the two frequencies type grating to form the zero-th image. Further, in the +side and −side of the zero-th image, the 20-th and 21-th diffraction images are formed at the positions which are apart from the 0-th image by 100 μm and 105 μm, respectively. According to the simulation result, the intensity values of the zero-th, ±20-th and ±21-th beams are substantially same level.

Figure 7:
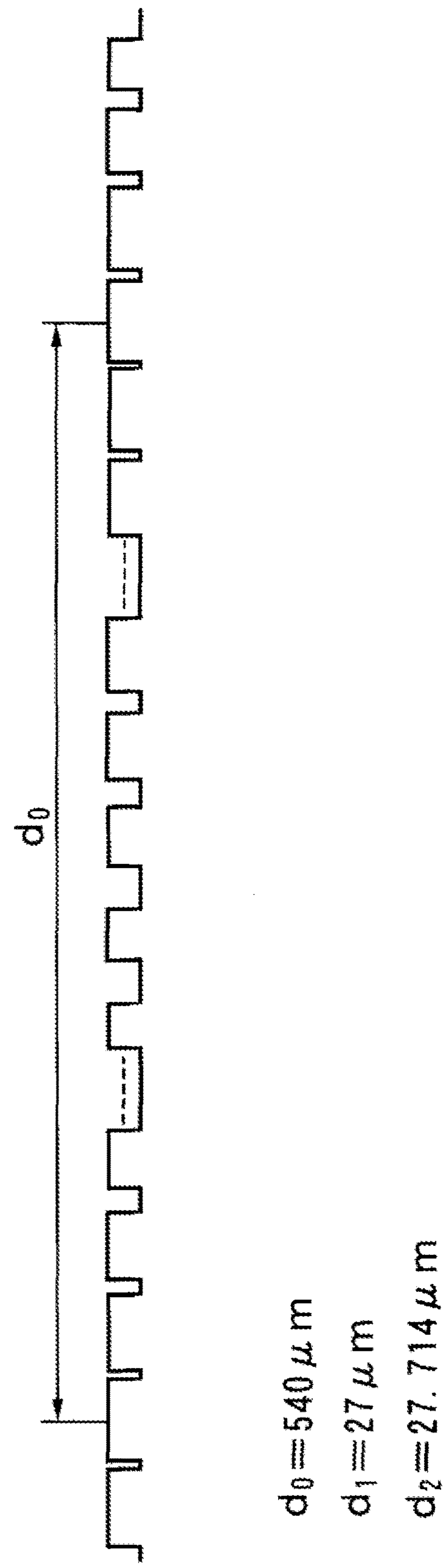
FIG. 7 is a view showing one example of a grating pattern of the two frequency type diffraction grating formed based on logical sum of the two spatial frequency components.

FIG. 7 denotes one example of the grating pattern of the phase diffraction grating of two frequencies type. In the present example, the grating pattern is formed by calculating the logical sum of the first spatial frequency (grating pitch: d1) and the second spatial frequency (grating pitch: d2) and by binarizing the obtained logical sum. In FIG. 7, the horizontal direction shows the position in the direction perpendicular to the grating groove and the vertical direction shows the depth of the grating groove. The basic period of the grating pattern is 540 μm, and the grating pattern is designed such that the duty ratio becomes 50% at a center of one period. Furthermore, in this example, the grating pattern is formed based on the logical sum, but it is possible to form the grating pattern on the basis of the logical product or exclusive OR of two spatial frequency components. The two frequencies type phase diffraction grating of reflection type according to the invention can be manufactured by the etching process using the lithography and by the multi-layer structure forming process. That is, the grating grooves having the depth of λ/4 are formed on a glass substrate based on the grating pattern of the composite waveform by etching process using the lithography, and then the reflection film of molybdenum layers and the silicon layers is formed on the glass substrate.

Figures 8A, 8B, 8C:
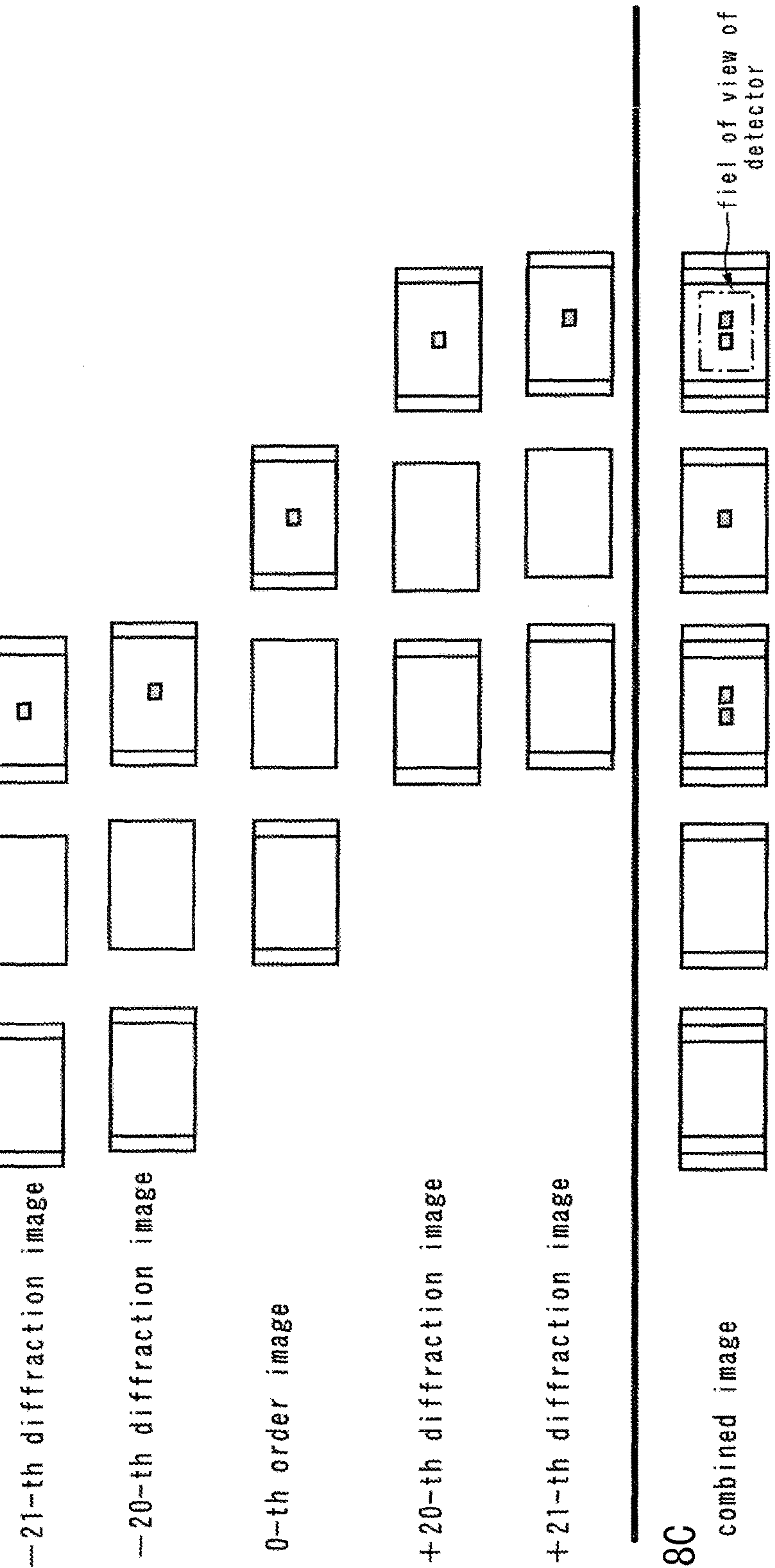
FIGS. 8A, 8B and 8C are views showing a combined images formed by the diffraction grating arranged in the imaging system.
Figure 9A:
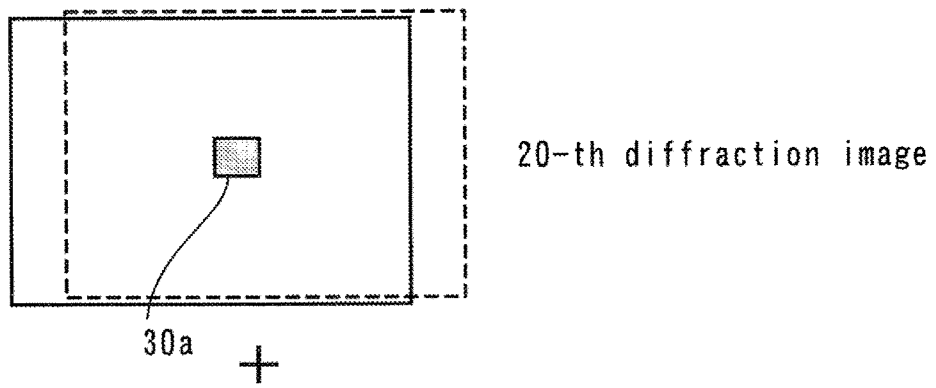
FIGS. 9A, 9B, 9C and 9D are views showing one example of the images formed in a field of view of an imaging device.
Figure 9B:
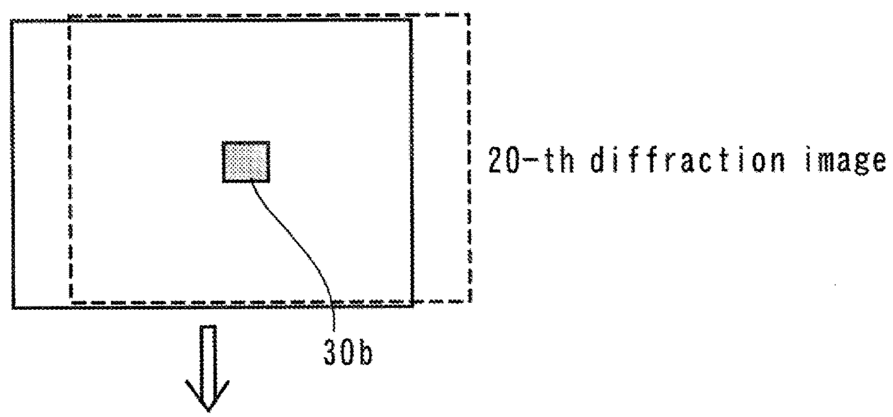
Figure 9C:
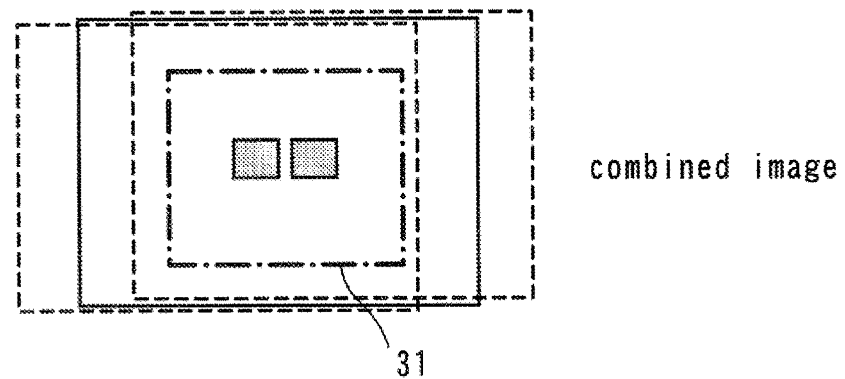
Figure 9D:
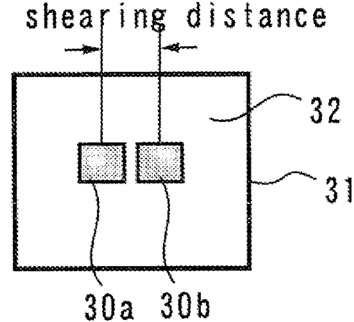

Then, the diffraction images which are formed on the detector (first image plane) by the third grating arranged in the imaging system will be explained. FIG. 8A illustrates three illuminated areas formed on the photomask, FIG. 8B illustrates diffraction images respectively formed on the detector by the 0-th, ±20-th and ±21-th diffraction actions of the third grating, and FIG. 8C illustrates a combined image formed on the detector. As shown in FIG. 8A, on the photomask, there is formed the 0-th diffraction image by the 0-th beam. In addition, on the +side of the 0-th diffraction image, the 20-th and the 21-th diffraction images are formed at the positions laterally shifted from the 0-th order image by 100 μm and 105 μm by the 20-th diffraction beam (first diffraction beam) and 21-th diffraction beam (second diffraction beam), respectively. These 20-th and 21-th diffraction images form a partially overlapped illumination area. And also, on the −side, the −20-th and −21-th diffraction images are formed at the positions laterally shifted by 100 μm and 105 μm, respectively. In the present example, the +20-th and +21-th diffraction beams are used as a first and second diffraction beams for the measurement, and the illuminated area where the first and second diffraction beams partially overlap each other is used for the measurement. Furthermore, the monitor pattern is suitably positioned so that its image is located within the illuminated area where the first and second diffraction beams overlap each other.

The reflected beams by three illuminated areas on the photomask strike the third diffraction grating, and the diffraction images shown in FIG. 8B is formed on the detector. At the center of the image plane, 0-th diffraction image of three illuminated areas is formed.

As the diffraction image on the +side, the diffraction image of three illuminated areas is formed by the 20-th diffraction beam (third diffraction beam) at the position where is laterally shifted from the 0-th image by 100 μm in the diffraction direction of +side. And also, at the position where is laterally shifted by 105 μm from the 0-th image, the diffraction image of three illuminated areas is formed by the 21-th diffraction beam (fourth diffraction beam). The +20-th and +21-th diffraction images are laterally sifted from each other by 5 μm and thus partially overlap each other.

As the diffraction image on the −side, the diffraction image of three illuminated areas is formed by the −20-th diffracted beam at the position where is laterally shifted from the 0-th image by 100 μm in the diffraction direction of −side. Further, at the position where is laterally shifted by 105 μm, the diffraction image of three illuminated areas is formed by the −21-th diffracted beam. The diffraction images of −20-th and −21-th are laterally sifted from each other by 5 μm.

The diffraction images of the 0-th, +20-th, +21-th, −20-th, and −21-th formed by the third diffraction grating are combined to form five images on the detector, as shown in FIG. 8C. Such five diffraction images are formed as separated images. In the present example, the diffraction images formed by the +20-th and +21-th diffraction action of the third grating are used for the measurement. Therefore, the stage is adjusted so that only the overlapped area of the +20-th and +21-th diffraction images is located within the field of view of the imaging device in order to measure the phase shift amount of the monitor pattern.

FIG. 9 denotes the diffraction images which are formed within the field of view of the imaging device and is used for the measurement. FIG. 9A illustrates the diffraction image formed by the +20-th diffraction beam emitted from the third grating (third diffraction beam), FIG. 9B illustrates the diffraction image formed by the +21-th diffraction beam (fourth diffraction beam), FIG. 9C illustrates the combined image formed by the +20-th and +21-th diffraction beams on the detector, and FIG. 9D illustrates the composite image formed within the field of view of the imaging device. The diffraction images formed by the third and fourth diffraction beams are partially overlapped each other on the imaging device. The +20-th and +21-th diffraction images respectively include the image of the monitor pattern and are laterally shifted from each other by the shearing amount. Therefore, as shown in FIGS. 9C and 9D, on the detector, there is formed a composite image including two monitor pattern images 30*a* and 30*b* which are shifted from each other by the shearing distance. Therefore, the position of the stage in X and Y directions is adjusted so that the two images of the monitor pattern 30*a* and 30*b* are located within the field of view 31 of the detector. FIG. 9D shows the captured image by the imaging device. The monitor pattern images 30*a* and 30*b* are an interference image consisting of the reflected beams by the monitor pattern and by the reflection film around the monitor pattern, and the image of the reflection film 32 around the monitor pattern image is an interference image consisting of the reflected beams by the reflection film. Therefore, the phase shift amount caused by the monitor pattern can be measured by comparing the phase states of the interference images of the monitor pattern and the reflection film with each other by use of the fringe-scan.

Figure 10A:
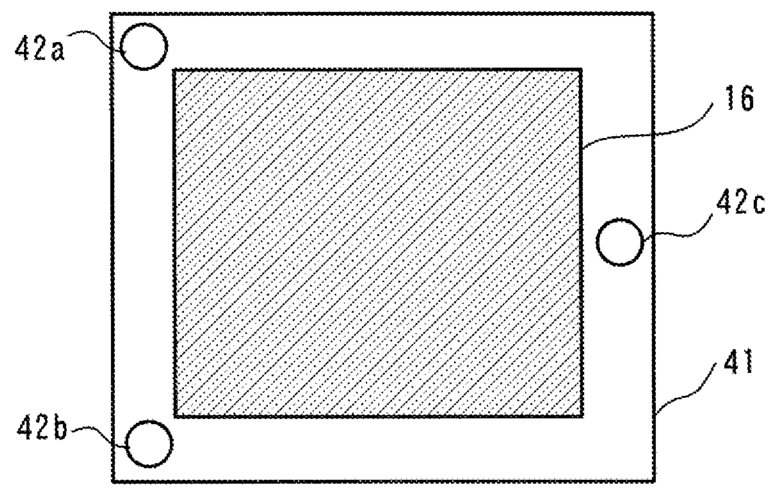
FIGS. 10A and 10B are views showing one example of a mask stage.
Figure 10B:
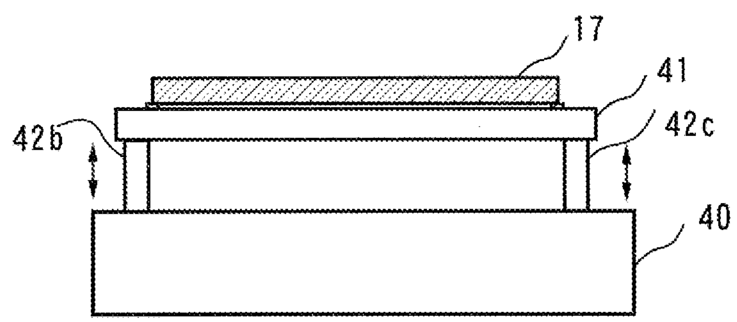

Then, the mask-stage supporting the photomask will be explained. FIG. 10 shows one example of the mask-stage, FIG. 10A is a diagrammatic plan view and FIG. 10B is a diagrammatic side view. The mask-stage comprises a X-Y stage 40 and a tilting stage 41. To the X-Y stage 40, the tilting stage 41 is connected via three actuators 42*a* to 42*c*, and the photomask 17 is arranged on the tilting stage. Three actuators displace in the arrowed direction. The actuators 42*a* and 42*b* displace along the same direction and the actuator 42*c* displaces along the opposite direction. That is, when the actuators 42*a* and 42*b* displace upward, the actuator 42*c* displaces downward, and when the actuators 42*a* and 42*b* displace downward, the actuator 42*c* displaces upward. Therefore, the center of the stage dose not displace and only the portions of right and left sides displace by equal amount each other. In this example, a horizontal position of the stage is a reference position. In this case, for example, by controlling the actuators such that the left side portion displaces upward and the right side portion displaces downward, the path-length difference of one period can be introduced between the first and second diffraction beams emitted from the second grating and thereby the fringe-scan can be performed.

As an example, when the shearing amount is set to 5 μm and the phase modulation amount of $2\pi$ is introduced, a height difference between two illuminated points is 6.75 nm. In this case, the angle variation of the photomask is 1.35 mrad. Such angle variation of the stage can easily be controlled by continuously changing the displacement of the actuators. According to the invention, during the fringe-scan, only the stage moves and all of the optical elements are kept in stationary state, and thereby the stable measurement can be performed.

Figure 11A:
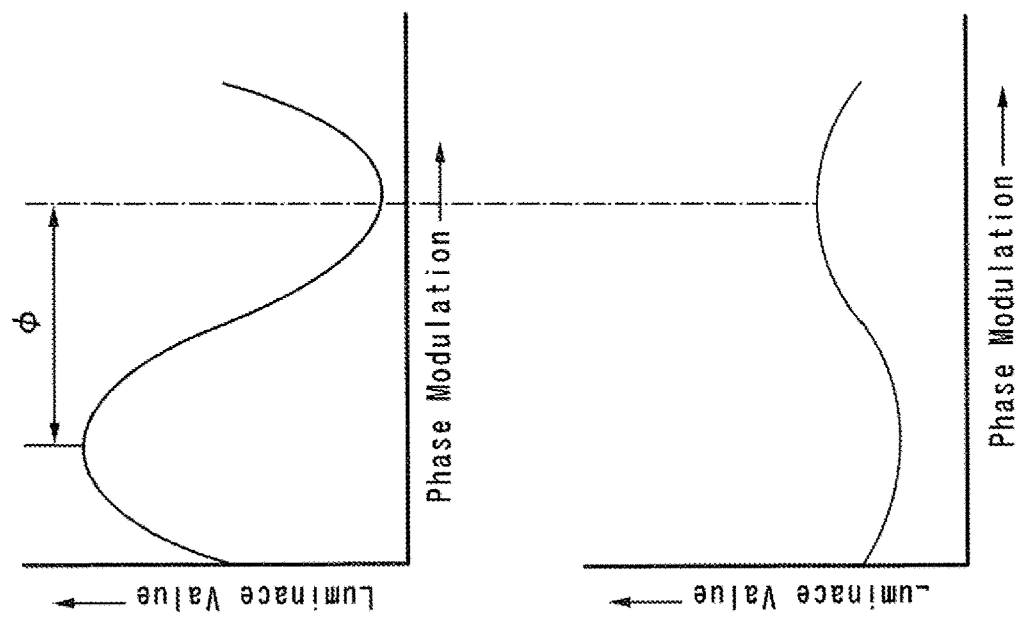
FIGS. 11A and 11B are views showing a measuring sequence for measuring the phase shift amount caused by the absorber pattern.
Figure 11A:
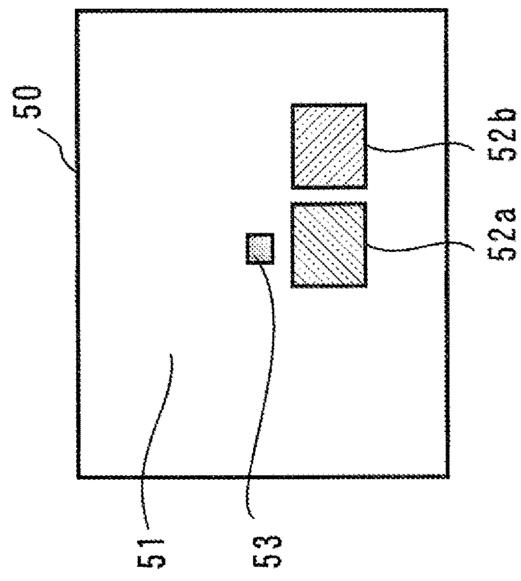
Figure 11B:
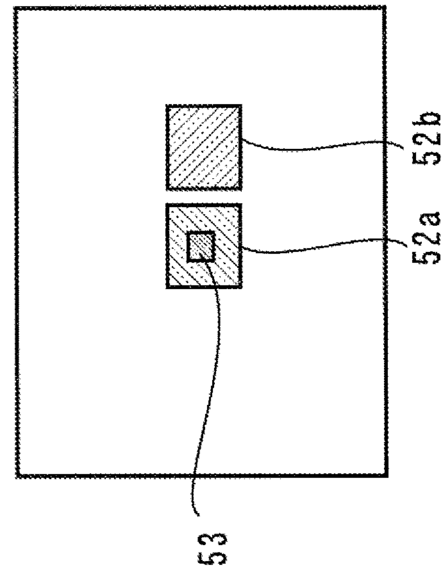

Subsequently, the measuring sequence of the phase shift amount caused by the monitor pattern will be explained. In FIGS. 11A and 11B, the left side diagrams denote the captured image by the imaging device, and the right side diagrams denote a relation between the phase modulation quantity introduced by the fringe-scan and the luminance value of the interference image. Referring to FIGS. 11A and 11B, the captured image 50 includes the interference image 51 of the reflection film and two interference images 52*a* and 52*b* of the monitor pattern. The interference image of the reflection film consists of the reflected beams by the reflection film, and the interference image of the monitor pattern consists of the reflected beams by the monitor pattern and by the reflection film.

Upon the measurement, a measuring area 53 comprising a plurality of pixels is set in the captured image 50. The measuring area 53 is positioned at the center of the captured image 50 and is smaller size than the monitor pattern image 52*a* and 52*b*. Then, the position of the photomask is adjusted in such a manner that two monitor pattern images 52*a* and 52*b* are located in the vicinity of the measuring area 53. In this state, the fringe-scan is performed using the tilting mechanism of the stage so as to introduce the phase modulation quantity of one period. That is, the fringe-scan or the phase modulation is performed by continuously changing the inclined angle of the stage to introduce the path-length difference between the first and second diffracted beams. The relation between the phase modulation quantity introduced by the fringe-scan and the luminance value of the interference image is shown in the graph of right side of FIG. 11. The phase modulation data shown in FIG. 11A denotes the modulation data of the interference image 51 of the reflection film, and such modulation data show the change of the phase difference between two reflected beams by two illuminated points on the reflection film, respectively. Such phase modulation data show the phase state inherent to the interferometer and can be reference data in the measurement of the phase shift amount. The phase modulation data can be formed by performing the fast Fourier transform (FFT) process for the output signal from the imaging device and the introduced phase modulation quantity by the fringe-scan.

Subsequently, as shown in FIG. 11B, the measuring area 53 is positioned within the interference image 52*a* or 52*b* of the monitor pattern by controlling the X-Y mechanism of the stage. In this state, the phase modulation of one period is performed by continuously changing the inclined angle of the stage. The right side graph of FIG. 11B shows the relation between the introduced modulation quantity and the luminance intensity of the monitor pattern image 52*a*. This interference image consists of the reflected beams by the monitor pattern and by the reflection film and includes the phase shift amount caused by the monitor pattern. Therefore, the phase shift amount $\phi$ caused by the monitor pattern can be measured by comparing the phase modulation data respectively shown in FIGS. 11A and 11B with each other. Specifically, by measuring the shift amount $\phi$ of the peak position of the phase modulation data of the monitor pattern image 52*a* shown in FIG. 11B on the basis of the peak position in phase modulation data of the reflection film image 51 shown in FIG. 11A, the phase shift amount of the monitor pattern can be measured. Therefore, using fast Fourier transform (FFT) means provided in the signal processor, two phase modulation data shown in FIGS. 11A and 11B are formed by performing the fast Fourier transform process for the image signal outputted from the imaging device and the introduced phase modulation quantity by the fringe-scan, and thereby the phase shift amount of the monitor pattern can be measured.

Figure 12A:
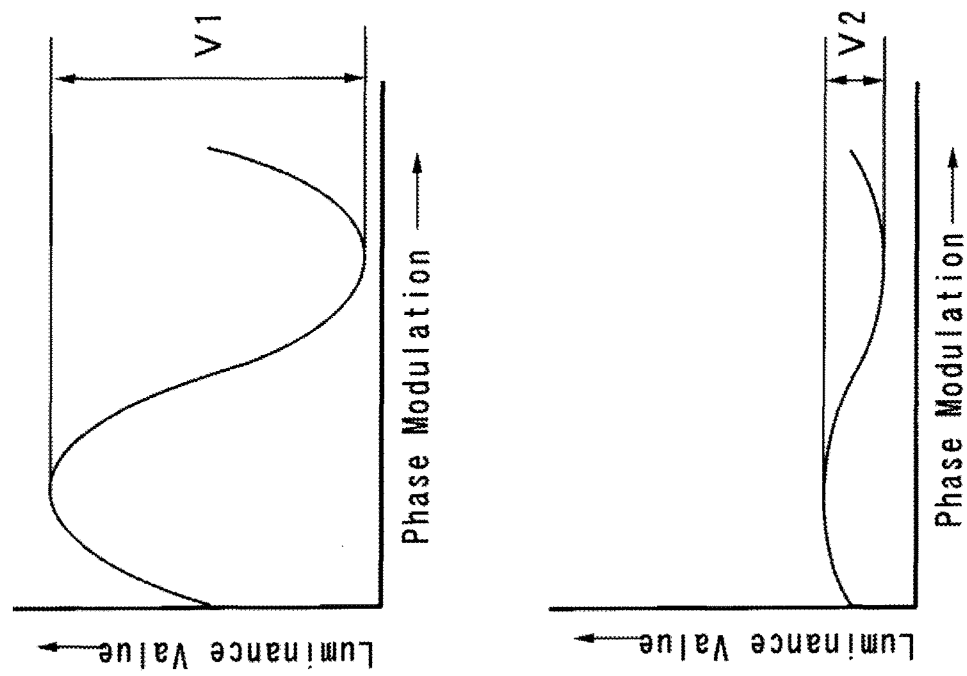
FIGS. 12A and 12B are views showing the measuring sequence for measuring the absorptivity of the absorber pattern.
Figure 12A:
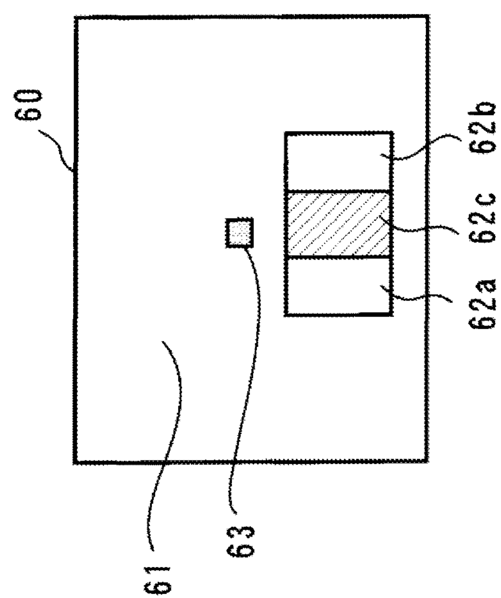
Figure 12B:
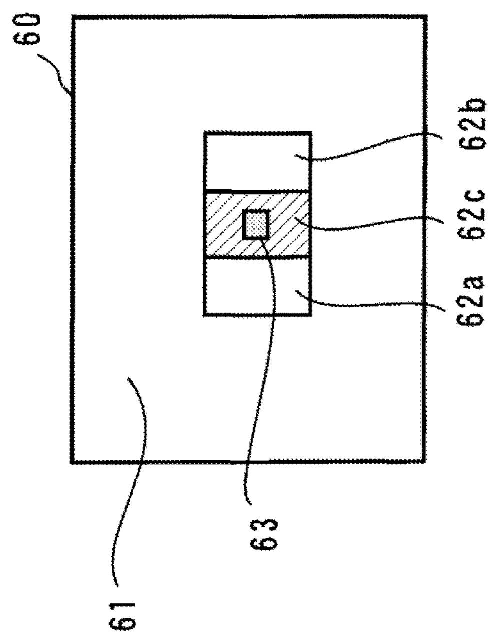

Next, the measurement of the absorptivity of the absorber formed on the reflection film will be explained. FIG. 12 illustrates the sequence of the absorptivity measurement of the absorber. When measuring the absorptivity of the absorber, the monitor pattern of the absorber having relatively large size is used in order to form a partially overlapped area of two interference images of the monitor pattern on the imaging device. In FIGS. 12A and 12B, the left side diagrams denote the captured image by the imaging device, and the right side diagrams denote the relation between the phase modulation quantity introduced by the fringe-scan and the luminance value of the interference image. Referring to FIGS. 12A and 12B, the captured image 60 includes the interference image 61 of the reflection film, two interference images 62*a* and 62*b* of the monitor pattern of the absorber and the overlapped area 62*c* of two monitor pattern interference images. If the size of the monitor pattern is set to be larger and the shearing distance is set to be relatively shorter, the overlapped area 62*c* consisting of two monitor pattern interference images 62*a* and 62*b* is formed. The measuring area 63 is set at the center of the captured image, and X-Y stage is adjusted so that the overlapped area 62*c* is located in the vicinity of the measuring area 63. In this state, the fringe-scan is performed to acquire the phase modulation data for the interference image 61 of the reflection film. The acquired modulation data is shown in the right side of FIG. 12A. Such modulation data is formed by the reflected beams by two illuminated areas on the reflection film.

Subsequently, as shown in FIG. 12B, the X-Y stage is adjusted so that the measuring area 63 is located within the overlapped area 62*c*. In this state, the fringe-scan is performed to acquire the phase modulation data for the interference image of the overlapped area 62*c*. The acquired data is shown in the right side of FIG. 12B. Such data are formed by the reflected beams by the absorber pattern.

Next, the fast Fourier transform process is performed to acquire amplitudes V1 and V2 of the modulation data of the interference image 61 of the reflection film and the interference image 62*c* of the monitor pattern shown in FIGS. 12A and 12B, respectively. Then, the absorptivity of the absorber pattern on the basis of the absorptivity of the reflection film can be obtained by dividing a squared value of the amplitude V2 by a squared value of the amplitude V1.

The present invention is not limited to the above-mentioned embodiments and can be modified and changed in various ways. For example, in the above-mentioned embodiments, the photomask of reflection type used for the EUVL was explained as an example, but it is possible to apply the present invention to measurement for the phase shift amount of a phase shifter of the photomask of transmission type. Further, in the above-mentioned embodiment, the phase grating of reflection type was used, but it is also possible to use the phase grating of transmission type.

What is claimed is:

1. An interferometer comprising:

an illumination source for generating an illumination beam, an illumination system for projecting the illumination beam emitted from the illumination source onto a sample so as to illuminate two areas of the sample where the two areas are laterally shifted from each other by a given distance, a detector for receiving radiation beams reflected by the two areas of the sample, and an imaging system for directing the radiation beams reflected by the two areas of the sample onto the detector, wherein said illumination system includes a first diffraction grating for diffracting the illumination beam emitted from the illumination source to produce first and second diffraction beams, wherein said two areas of the sample are illuminated by the first and second diffraction beams, respectively, and wherein said imaging system includes a second diffraction grating for diffracting the first and second diffraction beams reflected by the sample to produce a third and a fourth diffraction beams which are laterally shifted from each other, and wherein an interference image consisting of the third and fourth diffraction beams is formed on the detector, wherein said first and second diffraction gratings each comprise a phase diffraction grating for producing at least two higher order diffraction beams higher than zero-th beam, wherein said phase grating includes a grating pattern defined by two spatial frequency components, and wherein said grating pattern is defined by logical sum of the two spatial frequency components.

2. The interferometer of claim 1, wherein the first diffraction beam and the second diffraction beam generated by the first diffraction grating illuminate the two areas of the sample coherently.

3. The interferometer of claim 1, wherein said first diffraction beam and the second diffraction beam generated by the first diffraction grating are projected obliquely relative to a sample surface, and wherein said second diffraction grating diffracts the first diffraction beam and the second diffraction beam reflected by the sample surface.

4. The interferometer of claim 1, wherein the interference image formed on the detector includes phase difference information corresponding to a path-length difference between the first diffraction beam and the second diffraction beam generated by the first diffraction grating.

5. The interferometer of claim 4, wherein said interference image formed on the detector includes phase difference information corresponding to the variation in height of the sample surface.

6. The interferometer of claim 1, wherein the first and second diffraction gratings comprise a grating having the same structure, and wherein the first diffraction grating is arranged at a pupil position of the illumination system or in the vicinity of the pupil position, and the second diffraction grating is arranged at the pupil position or in the vicinity of the imaging system.

7. The interferometer of claim 1, wherein an objective system is arranged in the paths between the sample and the first and second diffraction gratings, and wherein the first and second diffraction beams emitted from the first diffraction grating are directed onto the sample through the objective system, and the first and second diffraction beams emitted from the sample are directed onto the second diffraction grating through the objective system.

8. The interferometer of claim 1, wherein a field stop is arranged in the path between the illumination source and the first diffraction grating to project the image of the field stop onto the sample.

9. The interferometer of claim 1, wherein said sample is supported on a stage having a tilting mechanism for tilting the sample, and wherein the tilting mechanism performs a fringe-scan for the first and second diffraction beams by scanning the tilted angle of the stage.

10. An interferometer comprising:

illumination source for generating an illumination beam, an illumination system for projecting the illumination beam emitted from the illumination source onto a sample so as to illuminate two areas of the sample where the two areas are laterally shifted from each other by a given distance, a detector for receiving radiation beams reflected by the two areas of the sample, and an imaging system for directing the radiation beams reflected by the two areas of the sample onto the detector, wherein said illumination system includes a first diffraction grating for diffracting the illumination beam emitted from the illumination source to produce first and second diffraction beams, wherein said two areas of the sample are illuminated by the first and second diffraction beams, respectively, and wherein said imaging system includes a second diffraction grating for diffracting the first and second diffraction beams reflected by the sample to produce third and fourth diffraction beams which are laterally shifted from each other, and wherein an interference image consisting of the third and fourth diffraction beams is formed on the detector, and wherein said first and second diffraction grating comprise a phase diffraction grating for producing at least two higher order diffraction beams higher than zero-th beam, and wherein said phase diffraction grating is a phase diffraction grating of reflection type comprising a substrate in which grating grooves having depth of $\lambda/4$ are formed based on the grating pattern and a reflection film formed on the substrate, $\lambda$ being a wavelength of the illumination beam.

11. The interferometer of claim 10, wherein a photomask of reflection type used in extremely ultraviolet lithography (EUVL) is used as the sample, and an EUV source whose emission peak wavelength is 13.5 nm is used as the illumination source.

12. An interferometer comprising:

an illumination source for generating an illumination beam, an illumination system for projecting the illumination beam emitted from the illumination source onto a sample so as to illuminate two areas of the sample where the two areas are laterally shifted from each other by a given distance, a detector for receiving radiation beams reflected by the two areas of the sample, and an imaging system for directing the radiation beams reflected by the two areas of the sample onto the detector, wherein said illumination system includes a first diffraction grating for diffracting the illumination beam emitted from the illumination source to produce first and second diffraction beams, wherein said two areas of the sample are illuminated by the first and second diffraction beams, respectively, and wherein said imaging system includes a second diffraction grating for diffracting the first and second diffraction beams reflected by the sample to produce third and fourth diffraction beams which are laterally shifted from each other, and wherein an interference image consisting of the third and fourth diffraction beams is formed on the detector, and wherein an objective system is arranged in the paths between the sample and the first and second diffraction gratings, and wherein the first and second diffraction beams emitted from the first diffraction grating are directed onto the sample through the objective system, and the first and second diffraction beams emitted from the sample are directed onto the second diffraction grating through the objective system, and wherein said objective system comprises a plane mirror and two concave mirrors, wherein a focus point of the objective system is set at infinity, and wherein one half area of the objective system forms a part of the illumination system and the remaining half area forms a part of the imaging system.

* * * * *